United States Patent [19]

Reinehr et al.

[11] Patent Number: 5,288,867

[45] Date of Patent: Feb. 22, 1994

[54] PROCESS FOR THE PREPARATION OF 2-HYDROXY-4,6-DIARYL-1,3,5-TRIAZINES

[75] Inventors: Dieter Reinehr, Kandern, Fed. Rep. of Germany; Jean-Pierre Bacher, Buschwiller, France

[73] Assignee: Ciba-Geigy Corporation, Ardsley, N.Y.

[21] Appl. No.: 11,931

[22] Filed: Feb. 1, 1993

[30] Foreign Application Priority Data

Feb. 4, 1992 [CH] Switzerland .................. 323//92

[51] Int. Cl.$^5$ .......................................... C07D 251/52
[52] U.S. Cl. ................................................. 544/219
[58] Field of Search ........................................ 544/219

[56] References Cited

U.S. PATENT DOCUMENTS 3,855,220  12/1974  Fischer ........................ 260/248
3,901,678   8/1975  Fischer ........................... 71/74

FOREIGN PATENT DOCUMENTS 2262188  7/1973  Fed. Rep. of Germany .

OTHER PUBLICATIONS

Alsofrom et al, J. Het. Chem. vol. 13, pp. 917–919 (1976).
Chemical Communications, 498 (1971).

Primary Examiner—John M. Ford
Attorney, Agent, or Firm—Kevin T. Mansfield; Edward McC.Roberts

[57] ABSTRACT

There is disclosed a process for the preparation of 2-hydroxy-4,6-diaryl-1,3,5-triazines, which comprises reacting the compound of formula

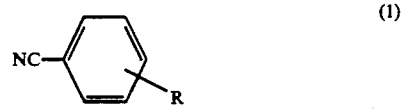

(1)

wherein

R is hydrogen, $C_1$–$C_4$alkyl or halogen, with urea, using a base selected from the class of the alkali metal hydrides, alkaline earth metal hydrides, or alkali metal amides, alkaline earth metal amides, or of the alkali metal $C_1$–$C_4$alcoholates in the presence of a polar solvent, to give the final products in a one step process in which the molar ratio of urea to base is 1:2 to 1:3 and the molar ratio of compound of formula (1) to urea is 2:1 to 5:1.

2-Hydroxy-4,6-diaryl-1,3,5-triazines are prepared in very good yield by the inventive process. The compounds are used as intermediates for the synthesis of UV absorbers.

6 Claims, No Drawings

PROCESS FOR THE PREPARATION OF 2-HYDROXY-4,6-DIARYL-1,3,5-TRIAZINES

The present invention relates to a novel simple process for the preparation of 2-hydroxy-4,6-diaryl-1,3,5-triazines starting from urea and aromatic nitriles.

The synthesis of 2-hydroxy-4,6-diaryl-1,3,5-triazines from urea and aromatic nitriles is known, inter alia from J. Heterocyclic Chem. 13, 917 (1976). In this reference, sodium hydride is used as base for the reaction. The molar amounts used in this process are always smaller than the corresponding amounts of urea.

Surprisingly, it has now been found that markedly higher yields can be obtained by using equivalent or larger amounts of base with respect to the urea.

Accordingly, the invention relates to a process for the preparation of 2-hydroxy-4,6-diaryl-1,3,5-triazines, which comprises reacting the compound of formula

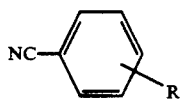

(1)

wherein

R is hydrogen, $C_1$-$C_4$alkyl or halogen, with urea, using a base selected from the class of the alkali metal hydrides, alkaline earth metal hydrides, or alkali metal amides, alkaline earth metal amides, or of the alkali metal $C_1$-$C_4$alcoholates in the presence of a polar solvent, to give the final products in a one step process in which the molar ratio of urea to base is 1:2 to 1:3 and the molar ratio of compound of formula (1) to urea is 2:1 to 5:1.

$C_1$-$C_4$Alkyl in the definition of R denotes those groups or moieties that contain 1 to 4, preferably 1 to 3, carbon atoms. Illustrative examples of such groups are methyl, ethyl, n-propyl, isopropyl, n-butyl, sec-butyl, tert-butyl, amyl, isoamyl or tert-amyl.

Halogen is preferably fluoro, bromo or chloro.

Typical examples of alkali metals are lithium, sodium or potassium. Sodium is preferred. Exemplary of alkaline earth metals are calcium and magnesium.

Suitable compounds of formula (1) are preferably those in which R is hydrogen, methyl or chloro.

Those compounds of formula (1) are especially preferred in which methyl and chloro are not ortho-positioned to the cyano group.

Illustrative examples of the compounds of formula (1) used in the practice of this invention are benzonitrile, m-tolunitrile, p-tolunitrile, p-chlorobenzonitrile or m-chlorobenzonitrile.

Illustrative examples of bases used in the process of the invention are lithium hydride, sodium hydride, potassium hydride, lithium amide, sodium amide, sodium methanolate or sodium ethanolate.

The reaction of the compound of formula (1) with urea is carried out in the presence of a polar solvent, typically dimethyl sulfoxide, dimethyl formamide or hexamethylphosphoric triamide. The preferred polar solvent is dimethyl sulfoxide.

The reaction time is from 2 to 24 hours, preferably from 2 to 8 hours. The reaction temperature is in the range from 20° to 70° C., the preferred range being from 30° to 60° C.

A particularly preferred embodiment of the invention comprises reacting the compound of formula

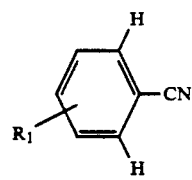

(2)

wherein
$R_1$ is methyl or chloro, with urea, using sodium amide as base in the presence of dimethyl sulfoxide, to give the final products in a one step process in which the molar ratio of urea to base is 1:2 to 1:3 and the molar ratio of compound of formula (2) to urea is 2:1 to 5:1.

The novel process makes it possible to prepare 2-hydroxy-4,6-diaryl-1,3,5-triazines in good yield and high purity. Compared with the known prior art processes, the reaction can be carried out at low temperature. The compounds obtained by the novel process are intermediates for the synthesis of UV absorbers.

The invention is illustrated by the following Examples.

Example 1: Preparation of 2-hydroxy-4-diphenyl-1,3,5-triazine with sodium amide

A mixture of 6 g (0.1 mol) of urea, 41.2 g (0.4 mol) of benzonitrile and 100 ml of dimethyl sulfoxide (DMSO) are charged to a reactor at 20° C. With stirring, 6 g (0.2 mol) of sodium hydride (80% in mineral oil) are then added, whereupon the temperature of the foaming mixture rises over c. 5 minutes to 44° C. Stirring is continued for 18 hours at room temperature and the reaction mixture is then poured into 200 ml of water acidified with 10 ml of glacial acetic acid. The precipitated product is filter-ed with suction and dried (25.8 g of a pale beige product). Recrystallisation from 1 10 ml of dimethyl formamide gives 20 g of the compound of formula

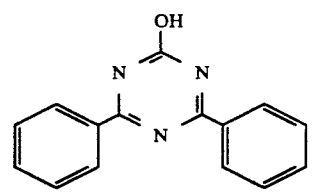

(101)

as an almost colourless powder.
Yield: 80% of theory
Mp: 297°–298° C.
Elemental analysis. found: 72.33% C; 4.63% H; 16.96% N calculated as $C_{15}H_{11}N_3O$: 72.28% C; 4.55% H; 16.86% N Example 2: Preparation of 2-hydroxy-4,6-diphenyl-1,3,5-triazine with sodium amide 12 g (0.2 mol) of urea are dissolved in 200 ml of dimethyl sulfoxide and to the solution are added 21.6 g (0.5 mol) of sodium amide (90%). The slightly exothermic reaction will rise the temperature to 30° C. The temperature is further raised to 50° C. and the reaction mixture is stirred for 18 hours at this temperature. After cooling to room temperature, 82.4 g (0.8 mol) of benzonitrile are added and the reaction mixture is stiffed for 4 hours at 50° C. The reaction mixture is then diluted with 500 ml of methanol, acidified with glacial acetic acid and filtered, giving 41 g of the compound of formula (101).

Yield: 82.2 % of theory.

Example 3: Preparation of 2-hydroxy-4,6-bis(4-methylphenyl)-1,3,5-triazine

The procedure described in Example 2 is repeated, except that 82.4 g (0.8 mol) of benzonitrile is replaced by 93.6 g of (0.8 mol) of p-tolunitrile. Conventional working up gives 38 g of a beige product which, after recrystallisation from 370 ml of dimethyl formamide, gives 29 g of a pale beige compound of formula

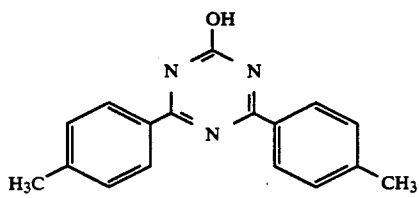
(102)

Yield: 68.5 % of theory
mp: >300° C.

Elemental analysis: found: 73.15% C; 5.49% H; 15.11% N calculated as $C_{17}H_{15}N_3O$: 73.63% C; 5.45% H; 15.15% N Example 4: Preparation of 2-hydroxy-4 6-bis(3-methylphenyl)- 1,3,5-triazine The procedure described in Example 2 is repeated, except that 82.4 g (0.8 mol) of benzonitrile is replaced by 93.6 g of (0.8 mol) of p-tolunitrile. Conventional working up gives 38 g of a beige product which, after recrystallisation from methyl cellosolve, gives 34.2 g of a pale compound of formula

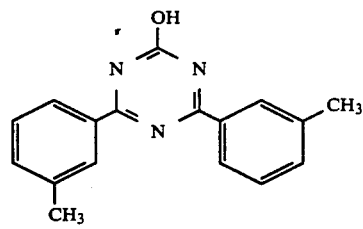
(103)

Yield: 61.7 % of theory
mp: 234°-234.5° C.

Elemental analysis: found: 72.84% C; 5.46% H; 15.24% N calculated as $C_{17}H_{15}N_3O$: 73.63% C; 5.45% H; 15.15% N; 5.77% O Example 5: Preparation of 2-hydroxy-4,6-bis(4-chlorophenyl)-1,3,5-triazine The procedure described in Example 2 is repeated, except that 82.4 g (0.8 mol) of benzonitrile is replaced by 100 g (0.72 mol) of p-chlorobenzonitrile. Conventional working up gives 62 g of a pale beige product which, after recrystallisation from dimethyl formamide, gives 50.5 g of a pale beige compound of formula

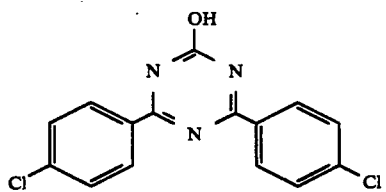
(104)

Yield: 79.5% of theory mp: >300° C.

Elemental analysis: found: 56.44% C; 2.84% H; 13.28% N; 22.02% Cl calculated as $C_{15}H_{19}Cl_2N_3O$: 56.63% C; 2.85% H; 13.21% N; 22.29% Cl Example 6: Preparation of 2-hydroxy-4 -bis(3-chlorophenyl)-1,3,5-triazine The procedure described in Example 2 is repeated, except that 82.4 g (0.8 mol) of benzonitrile is replaced by 100 g (0.72 mol) of m-chlorobenzonitrile. Conventional working up gives 52 g of a pale product which, after recrystallisation from methyl cellosolve and dimethyl formamide, gives 27.6 g of a pale beige compound of formula

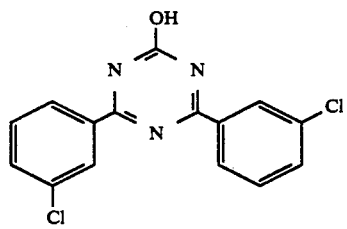
(105)

Yield: 43.4 % of theory
mp: 286°-287° C.

Elemental analysis: found 55.91% C; 2.98% H; 13.14% N; 21.63% Cl calculated as $C_{15}H_{19}Cl_2N_3O$: 56.63% C; 2.85% H; 13.21% N; 22.29% Cl

What is claimed is:

1. A process for the preparation of a 2-hydroxy-4,6-diaryl-1,3,5-triazine, which comprises reacting the compound of formula $$NC-\overset{3}{\underset{4}{\bigcirc}}-R \qquad (1)$$

wherein

R is hydrogen, $C_1$-$C_4$alkyl or halogen bound to phenyl in the 3- or 4-position, with urea, using a base selected from the class of the alkali metal hydrides, alkaline earth metal hydrides, or alkali metal amides, alkaline earth metal amides, or of the alkali metal $C_1$-$C_4$alcoholates in the presence of a polar solvent, to give the final product in a one step process in which the molar ratio of urea to base is 1:2 to 1:3 and the molar ratio of compound of formula (1) to urea is 2:1 to 5:1.

2. A process according to claim 1, wherein R is formula (1) is a hydrogen, methyl or chloro.

3. A process according to claim 1, wherein the reaction is carried out in the temperature range from 20° to 70° C.

4. A process according to claim 1, wherein the reaction time is from 2 to 24 hours.

5. A process according to claim 1, wherein the polar solvent is selected from the group consisting of dimethyl sulfoxide, dimethyl formamide and hexamethylphosphoric triamide.

6. A process according to claim 1, which comprises reacting the compound of formula

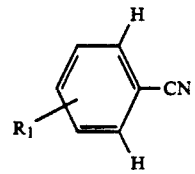

wherein
$R_1$ is methyl or chloro, with urea, using sodium amide as base in the presence of dimethyl sulfoxide, to give the final product in a one step process in which the molar ratio of urea to base is 1:2 to 1:3 and the molar ratio of compound of formula (2) to urea is 2:1 to 5:1.

* * * * *